United States Patent [19]

Johnston

[11] 4,200,980
[45] May 6, 1980

[54] ORTHODONTIC FORMULATION AND METHOD

[75] Inventor: Reece W. Johnston, Fort Worth, Tex.

[73] Assignee: Advance Dental Corporation, Fort Worth, Tex.

[21] Appl. No.: 883,408

[22] Filed: Mar. 6, 1978

[51] Int. Cl.² ............................................... A61C 7/00
[52] U.S. Cl. .......................................... 433/8; 433/228
[58] Field of Search .......................... 32/14 A, 14 C, 8

[56] References Cited

U.S. PATENT DOCUMENTS

| | | | |
|---|---|---|---|
| 3,955,282 | 5/1976 | McNell | 32/14 C |
| 4,010,545 | 3/1977 | Kilian | 32/14 A |

*Primary Examiner*—Robert Peshock
*Attorney, Agent, or Firm*—Wm. T. Wofford

[57] ABSTRACT

A composition and method for affixing a dental appliance to the teeth characterized by effecting a layer of catalyst that will effect polymerization of a bonding resin on the surface of the teeth to which the dental appliance is to be affixed, after the surface has been cleaned and dried so as to effect a good bond; effecting a layer of the catalyst on the base of at least a portion of the dental appliance that is to be bonded to the teeth after the base has been cleaned and dried so as to effect a good bond; positioning the base of the portion of the dental appliance adjacent the teeth after resin has been applied intermediate the two layers of catalyst on the base and on the surface of the tooth. After a predetermined cure time, the remainder of the dental appliance is affixed in place. The bonding resin is selected from the group consisting of epoxy, per se or capped with hydrolysis-resistant moiety; urethane; cyano-acrylate; methacrylate; vinyl ester; and acrylate. Appropriate catalyst such as benzoyl peroxide and initiator are preferably employed for effecting polymerization. Also, critical viscosity of the bonding resin in the range of 25,000-40,000 centipoises, as measured with a Brookfield Niscometer at 50° C., is employed, with filler if necessary, to obtain the desired wettability and prevent "creep" during gellation. Also disclosed are preferred constituents and steps in the method, including the indirect bonding method.

22 Claims, 3 Drawing Figures

ORTHODONTIC FORMULATION AND METHOD

BACKGROUND OF THE INVENTION

1. Field of the Invention

This invention relates to method and composition for affixing a dental appliance to teeth. More particularly, this invention relates to method and composition for bonding directly to the teeth to facilitate affixing a dental appliance thereto.

2. Description of the Prior Art

The prior art has seen a wide variety of orthodontic corrective procedures to align mal-occluded teeth in humans and the like. Most of these corrective procedures employed a dental appliance in one way or another to correct improper growth of the teeth and the like. The term "dental appliance" is employed in its broad sense in this application to signify any of the appliances whether to correct the growth of teeth, bridging of the teeth and the like. Such dental appliances typically include braces, space maintainers, splints, bridge works of more elaborate type and any other type of device that will be affixed to one or more of the teeth in the mouth with the objective of supporting or affecting the action or growth of other teeth.

A major orthodontic corrective procedure to align mal-occluded teeth is the placement of metal bands around individual teeth and thereafter affixing the remainder of the dental appliance to these metal bands. The metal bands may have affixed bases or brackets, sometimes referred to as the fixed appliance, or part thereof. Wires having high-tensile strength are then attached to the metal bands and the fixed portion of the appliance and then to the remainder of the appliance and teeth to affect proper tooth movement through the action of the wire itself or of springs or spurs attached to the wire. The affixed appliances, or brackets, require precise positioning to effect proper tooth movement.

Adhesive bonding of the affixed appliances to tooth surfaces is the ultimate in this type of orthodontic practice in order to eliminate the tedious band fitting procedure and to greatly reduce the decalcification of teeth and the gingival damage that all too frequently occurs with banding. Moreover, bonding with a resin type adhesive facilitates cleaning by the patient with less opportunity for food accumulation and consequent tooth decay compared to the banding because most of the appliances are at the front surface of the teeth in adhesive bonding with greater accessibility for cleaning.

Despite the advantages of adhesive bonding, it has not achieved universal success because of the inconsistent results from the currently available bonding orthodontic adhesives and the techniques, or methods, of using them.

Currently available orthodontic bonding adhesives generally use one of two techniques for applying orthodontic appliances to the teeth. In each of the techniques the teeth are prepared by cleaning, acid etching, washing and drying.

In the first technique, the bonding resin co-monomer is not mixed with a catalyst but is applied to a clear, transparent plastic bracket that is precisely positioned on the dried tooth surface. An ultraviolet light is directed onto the clear bracket so as to penetrate through to initiate polymerization of the bonding resin. In this way, the viscosity of the resin co-monomer can be adjusted to optimize wetting and avoid creeping but the requirement for a clear, light-penetrating material for a bracket limits the strength of the bracket, which are generally inferior to the stainless steel brackets otherwise employed. Consequently there are frequent failures due to inadequate structural strength to resist the stress of the attachment; for example, force by high-tensile strength wire. The ultraviolet light itself, if used indiscriminately, is known to produce skin cancer, especially on soft tissue. Consequently, many orthodontists favor another procedure.

Another procedure comprises admixing the exact proportions of an adhesive formulation consisting of filler, catalyst, co-monomer resin and accelerater on a cold plastic slab, or glass plate and the like. The mixing of the catalyst and co-monomer initiates polymerization of the co-monomer resin immediately so the orthodontist has limited working time to coat the several bases of the brackets, or portion of the appliance to be bonded to the teeth, and to precisely position it on the prepared teeth surfaces. Also, the viscosity of the resin is continuously changing with the degree of polymerization. This affects positioning and creep of the brackets, as well as the ultimate bond strength. Viscosity also varies as the proportions of resin and catalyst are varied, deliberately or carelessly. For example, if the amount of catalyst in relation to the resin is too large, polymerization is too rapid and the higher viscosity of the resulting resin will cause inadequate wetting of the surfaces of the teeth and bracket base. Good wetting onto clean surfaces is the most important criterion in forming strong bonds. The result is a weak bond at best and ultimate displacement of the appliance from the tooth. On the other hand, if the proportion of catalyst is too small, the resulting mixture prepared by the orthodontist or his assistant has a low viscosity due to slow polymerization. This results in "creeping" of the appliance from its optimum placement position on a respective tooth. If attempts are made to reposition a bracket, or portion of an appliance, after "creep," then the bond is weakened and the appliance will ultimately be displaced from the tooth.

From the foregoing, it can be appreciated, that the prior art has not been totally satisfactory in solving the problems. First, a thorough mixing of exactly the right proportions of the adhesive is a requirement in order to evenly disperse the catalyst. Second, even a properly proportioned admixture forces the orthodontist to work in a limited time frame without the luxury of being able to correct for unanticipated delays or contingencies. Otherwise he must begin anew, with wasting of time and expensive adhesive.

Idealy, a bonding method and formulation would have the following features:

1. The bonding formulation and method should avoid the use of ultraviolet light or carcinogenic agents.

2. The bonding method or composition should allow relative freedom of the dentist to be as precise in placement and as careful in maintaining the bracket, or base of a dental appliance, in position to avoid creep as he wishes, without having to work within a time constraint.

3. The bonding method and composition should provide a relatively constant viscosity that is optimal for effectively wetting the surfaces of the teeth and of the dental appliance that is to be bonded to the teeth; simultaneously avoiding creep of the bracket, or portion of the dental appliance to be bonded to the teeth.

4. The bonding method and composition should obviate the necessity for careful admixing of predetermined portions so as to be operable even at moments of carelessness by the orthodontist or assistant.

5. In specific embodiments, the bonding method and composition should be operable by either direct bonding or indirect bonding techniques if the latter are desired to speed up the affixing of the dental appliance.

6. Moreover, in specific aspects, the bonding method and composition should provide a means that will facilitate application of one or more of the ingredients to the portion of the dental appliance that is to be bonded to the teeth to eliminate the care of having to wet that portion of the dental appliance.

7. The bonding method and composition should facilitate using complementary advantageous method steps; such as, forming shields or sealant layers, over the teeth to minimize decay.

SUMMARY OF THE INVENTION

Accordingly it is an object of this invention to provide a bonding method and composition for bonding a dental appliance to teeth that has one or more of the foregoing features not heretofore provided by the prior art, while alleviating the disadvantages of the prior art.

It is another object of this invention to provide a method and composition for bonding a dental appliance to teeth that has a plurality of the features delineated hereinbefore as desirable and not heretofore provided by the prior art, simultaneously accomplishing the preceding object.

It is a still further object of this invention to provide, in specific embodiments, a method and composition of bonding a dental appliance to the teeth that has all of the features hereinbefore delineated as being desirable and not hereinbefore provided by the prior art, while at the same time, alleviating the disadvantages of the prior art.

These and other objects will become clear from the descriptive matter hereinafter, particularly when taken in conjunction with the appended drawings.

In accordance with one aspect of this invention, there is provided a method of affixing a dental appliance to at least one tooth in the mouth comprising for each such tooth a plurality of steps of:

a. effecting a layer of catalyst that will effect polymerization of a bonding resin to a preselected surface area of the tooth to which the dental appliance is to be bonded, the surface being cleaned and dried so as to effect a good bond;

b. effecting a layer of catalyst on the base of at least a portion of the dental appliance that is to be bonded to the teeth, the base having been cleaned and dried so as to effect a good bond;

c. positioning at least a portion of the dental appliance that is to be bonded to the surface of the tooth adjacent the surface of the tooth with a layer of a bonding resin disposed between the two layers of catalyst on, respectively, the portion of the dental appliance and the tooth so as to sandwich the thin layer of bonding resin between the two layers of catalyst and obtain polymerization of the resin and the necessary bonding of the base of the dental appliance to the tooth; and d. after a predetermined cure time sufficient to obtain curing of the bonding resin, affixing the remainder of the orthodontic appliance.

In another aspect of this invention, there is provided a composition for affixing a dental appliance to a tooth comprising:

a. a bonding resin and, admixed with the resin, sufficient filler to obtain a viscosity in the range of 25,000–40,000 centipoises at 50° C.; and b. in a separate container, a catalyst for effecting polymerization of the resin to form a cementitious and durable bond between the base of the dental appliance and the tooth.

In both the method and composition, the bonding resin is selected from a class consisting of epoxy resin, per se, or capped with hydrolysis-resistant moieties such as the acrylic or methacrylate moieties; urethane resin; cyanoacrylate resin; methacrylate resin; vinyl ester resin; and acrylate resin. The filler that is employed to obtain the critical viscosity comprises small particles of alumina, calcium fluoride, glass, asbestos, or silica. The particle sizes are from colloidal sizes up to 35 microns with no particle size large enough to interfere with the bonding.

DESCRIPTION OF THE PREFERRED EMBODIMENT(S)

The descriptive matter immediately hereinafter is arranged so as to describe the materials that have been referred to in respective method steps. Accordingly, the first descriptive matter will be clarifying what is meant by the respective bonding resins and catalysts delineated in the Summary of the Invention hereinbefore.

The bonding resins that are employed in this invention are those resins that will bond in the presence of a catalyst to form a firm, substantially permanent bond that resists hydrolysis, even in the presence of mouth acids and enzymes in the mouth. The bond that is formed, as well as the catalyst and bonding resin should be nontoxic so that the patient is not adversely affected during the bonding of the dental appliance onto the teeth or the retention of the appliance in the mouth. These types of bonding resins are conventionally available and include the epoxy resin, per se, or capped with hydrolysis-resistant moieties; urethane resin; cyanoacrylate resin; methacrylate resin; vinyl ester resin; and acrylate resin. If desired, the resins that have ends that do not resist hydrolysis by their own chemical nature are capped with hydrolysis-resistant moieties such as the acrylate moiety or methacrylate moiety. Both the uncapped resins such as epoxy resins and methacrylic capped epoxy resins are commercially available, as from DuPont, Wilmington, Del.; Dow Chemical Company, Midland, Mich.; Shell Chemical Co., Houston, Tex.; or Rohm and Haas Chemical Company, St. Louis, Mo. If desired, the resin like the methacrylate capped epoxy resin may have other monomers such as styrene incorporated into its formulation in order to block hydrolysis of the ester linkage by steric hindrance. To ensure complete understanding, the following structural formula is given to amplify the definition of the epoxy resins. These resins are defined by the structural formula I.

To eliminate the harmful effects of epoxy curing agents the epoxide ends are reacted with the methacrylic moiety shown in formula II.

The methacrylic groups require harmless curing agents to effect polymerization.

Ordinarily, it is preferred to employ diluents to obtain clearer, less viscous monomer solutions. These diluents include styrene, methyl methacrylate, hydroxy methyl methacrylate, ethylene glycol dimethacrylate, diethylene glycol dimethacrylate, triethylene glycol dimethacrylate, various polyethylene glycol methacrylates individually, trimethylol propane-trimethacrylate, 1,4-butane glycol dimethacrylate, 1,3-butane glycol dimethacrylate, n-propyl methacrylate, n-butyl methacrylate, penta-erythritol tetra methacrylate, and the like. The preferred resin is methacrylate capped epoxy diluted with styrene constituting 40-55 percent of the final admixture.

In these epoxy resins, the value of n is selected such that the molecular weight will be in the range of 10,000-300,000, although it may be even higher to obtain the desired viscosity with lesser amount of filler, as described hereinafter.

The polymerization of these types of bonding resins is ordinarily effected by free radical initiation employing suitable initiators, or accelerators, as well as catalyst.

Typical of the initiators are amines such as N,N-dimethyl-para-toluidine; N,N-dimethylaniline; and cobalt naphthenate. As is recognized, the cobalt naphthenate is ordinarily employed with methyl ethyl ketone peroxide catalyst for the epoxide type resins. The preferred initiator is N,N-dimethyl-p-toluidine.

The catalyst may comprise any of those that are ordinarily employed for polymerizing these type of monomers. The preferred catalyst for this invention is either benzoyl peroxide or methyl ethyl ketone peroxide.

In accordance with this invention, there is no need to mix a powdered catalyst with a resin to form an admixture that changes viscosity and consistency during application. Instead, the resin may be formulated to have the desired critical viscosity in the range of 25,000-40,000 centipoises measured at 50° C. The optimum viscosity is about 32,000 centipoises (±ten percent). This viscosity is unchanging, therefore the working time allowed the orthodontist is essentially limitless, since there is no polymerization until the layer of bonding resin is emplaced between the two layers of catalyst on, respectively, the tooth and the base of the bracket, or portion of the appliance that is to be bonded to the teeth.

In order to obtain the viscosity as defined hereinbefore it is preferred to add an inert filler, in the form of a particulate solid. Preferably, the particles of solid have a predominant size of smaller than 35 microns with no sizes so large as to interfere with proper bonding between the appliance and the teeth. The filler is selected from the group consisting of alumina, barium fluoride, calcium fluoride, glass, asbestos, and silica. Of these, the colloidal silica such as formed by fumed silica is preferable. Thus the optimum viscosity of the bonding resin liquid can be formulated to allow being emplaced intermediate the two layers of catalyst on the appliance and the teeth surfaces that are to be bonded together.

To facilitate effecting a layer of catalyst on the cleaned dried surfaces of the dental appliance and the teeth that are to be bonded together, it is preferred to employ the catalyst in a solution of a drying agent. The drying agent is selected from the group consisting of methyl ethyl ketone, ethyl alcohol, acetone, ethyl ether, 2-methoxyethanol (methyl Cellosolve), 2-ethoxyethanol (ethyl Cellosolve), 2-propoxyethanol (propyl Cellosolve), 2-butoxyethanol (butyl Cellosolve) and admixtures thereof. The preferred admixture comprises about equal parts of methyl ethyl ketone and ethyl alcohol. In this way when the solution of the drying agent and catalyst are brushed onto or otherwise applied to the surface of the teeth or the surface of the dental appliance that is to be bonded to the teeth, the drying agent dries rapidly leaving a layer of catalyst on the surface that is to be bonded.

The drying agent may also contain a small concentration of silane to aid in bonding the dental appliance to the tooth enamel. A number of silanes can be employed, the preferred one is a solution comprising about 45 percent by weight of methanol or ethanol, with the silane being one such as Dow Corning's XZ-8-5069 silane.

Typically the bonding resin has employed therein a concentration of initiator in the range of 0.5-3.0% by weight. The optimum concentration of initiator is about 1.5-2.0% by weight of initiator in the bonding resin.

The concentration of the filler in the bonding resin may vary depending upon the type of filler and bonding resin being employed. With larger filler of, for example, −325 mesh U.S. Standard Sieve, up to 80 percent by weight of filler may be employed. Ordinarily, with colloidal size filler, the concentration of filler will be in the range of 4-10% by weight of the bonding resin. The optimum concentration of the filler would be in the range of 6-7% by weight of the preferred filler in the preferred resin to obtain the optimum viscosity of about 25,000-40,000 centipoises measured at 50° C.

When the catalyst is employed in the drying agent, it is preferable to employ a concentration of catalyst within the range of 1-20% by weight. The optimum concentration of the catalyst in the drying agent is about 7-8% by weight.

Where silane is employed in the drying agent, it is employed in a concentration in the range of 0.01-3% by weight; with the optimum concentration being about 0.05% by weight.

The cure time is in the range of about 10 minutes to about 2 hours for the bonding resin to develop sufficient strength to take the stress attendant to affixing of the remainder of the dental appliance. Ordinarily about 15-20 minutes are allowed before the orthodontist, or dentist begins to affix the remainder of the dental appliance.

Ordinarily an orthodontic appliance may comprise a series of mounting brackets that are to be bonded directly to surfaces of the teeth and the remainder of the appliance is high strength wire, connecting the brackets in a manner such as to apply torque or forces to the teeth to effect the desired movement of the teeth. The bases of the brackets are bonded to the teeth by one of two methods preparatory to affixing the remainder of the dental appliance. The first is referred to as the direct bonding method. The second is referred to as the indirect bonding method and is employed to expedite affixing the dental appliance to the teeth.

In direct bonding, the method of this invention is performed independently for each tooth involved. A multiplicity of steps is involved for each of the surfaces of the teeth to which a particular and respective bracket is to be bonded. For each tooth to be treated, the method comprises the steps of:

a. cleaning the surface of the tooth to which the bracket is to be affixed;

b. acidizing the surface of the tooth to which the bracket is to be affixed to create an etched surface;

c. water washing the acid-etched surface of the tooth to ensure it has been thoroughly cleaned;

d. drying the tooth with clean warm air;

e. applying a drying agent and a layer of catalyst on the cleaned, etched, dried tooth surface;

f. applying the catalyst to the cleaned base of the bracket;

g. applying the bonding resin to the layer of catalyst on the bracket base;

h. positioning the bracket base adjacent the surface of the tooth with the intermediate layer of resin between the two layers of catalyst on, respectively, the bracket base and the tooth so as to sandwich the thin layer of bonding resin between the two layers of catalyst and obtain polymerization of the bonding resin and the necessary bonding of the bracket to the tooth;

i. repeating the above described steps for each of the several teeth involved;

j. after a predetermined cure time, affixing the remainder of the dental appliance to the brackets.

Figure 1:
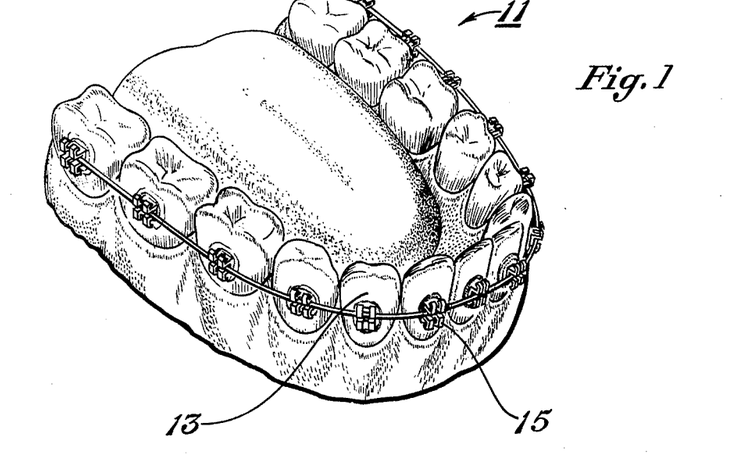
FIG. 1 is an isometric view of a dental appliance bonded to teeth in the mouth.
Figures 2, 3:
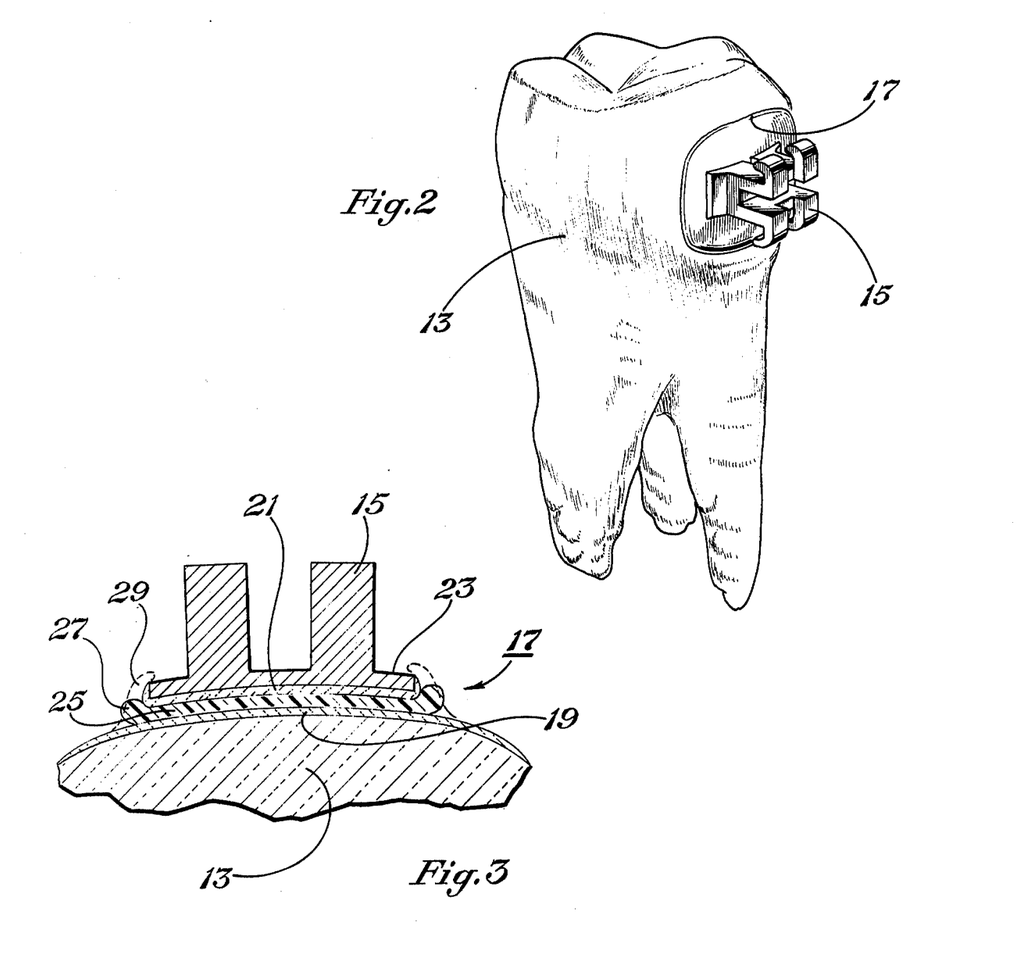
FIG. 2 is an isometric of a tooth having a bracket bonded thereto in accordance with FIG. 1.
FIG. 3 is a partial cross sectional view of the base of the bracket bonded to the surface of the tooth.

The method steps may be understood completely by referring to the accompanying FIGS. 1-3 in conjunction with the following descriptive matter.

FIG. 1 illustrates a dental appliance 11 applied to the teeth 13 by way of brackets 15. Each of the bases of the brackets are adhered to the surface of the teeth by a durable bond 17, FIG. 2. The bond 17, FIG. 3, is formed initially by a first layer 19 of catalyst on the surface of the teeth, a second layer 21 of catalyst on the base 23 of the brackets 15, and a third layer 25 of resin. As will be appreciated, the catalyst will initiate propagation of polymerization of the resin to form the final bond.

In carrying out the method of the invention, the dentist, the orthodontist, or the assistant first cleans the teeth with a suitable material such as a pumice type material in the form of a tooth paste or the like. Such pumices and pastes are conventionally employed and need not be described in great detail herein. The pumice type paste is then washed from the teeth with water and the teeth dried by warm clean dry air. Next an acid etch is applied to the teeth. Ordinarily phosphoric acid having a concentration in the range of 30-50 percent by weight is dabbed onto the teeth with a cotton pellet or light brush. After about a minute and a half, the teeth are rinsed with water again and dried with air.

In the preferred embodiment of this invention, the teeth are thereafter brushed with a solution of drying agent containing the catalyst in the indicated concentration to effect the layer of catalyst. In the particularly preferred embodiment, the solvent is about a 50-50 mixture of methyl ethyl ketone and ethyl alcohol so that it vaporizes rapidly leaving the catalyst in a layer on the surfaces of the teeth to which the bracket bases are to be bonded.

Next the cleaned metal brackets are arrayed on an absorbent towel. Preferably, a bracket is selected to have a curvature of the base to match the curvature of the surface of the tooth to which it will be adhered. A solution of the drying agent containing the catalyst is applied to the bases of the brackets. The surfaces of the bases of the bracket and the teeth are allowed to dry leaving the catalyst thereon.

If desired, as indicated hereinbefore, the delineated concentration of silane may be incorporated into the drying agent containing the catalyst to improve the wettability characteristics of the surfaces on which are effected the layers of catalyst.

Also as indicated, the bases of the respective brackets will have been cleaned of all dirt and grease. Grease is particularly detrimental to the effecting of a durable bond by the resin since it limits the bonding to the surfaces. A preferred technique is to store the inert bracket, such as the stainless steel brackets in a jar of the drying agent containing the catalyst, alone or with the silane and thereafter removing them with clean stainless steel forceps as they are needed, allowing them to dry on a clean absorbent surface. The drying agent vaporizes in 5 to 10 seconds, and a layer of catalyst is left in place for effecting bonding once the resin has been emplaced on a base before it is emplaced on a tooth.

The bonding resin is prepared by inclusion of the desired amount of filler to obtain the desired viscosity in the delineated range. The preparation may be by the orthodontist or the manufacturer, as in a pre-prepared admixture specifically for bonding a bracket to a tooth.

When all the brackets and teeth have been prepared and are ready for bonding, the orthodontist or assistant places a small amount of the bonding resin of the desired viscosity on the surface of the base of the bracket with either a spatula or a dispensing device (such as a tube, syringe or the like). Thereafter, the bracket is positioned on the teeth in exact location desired with the firm layer of resin sandwiched between the two layers of catalyst. The bracket is pushed firmly against the teeth for close contact, where by virtue of the viscosity of the resin the bracket will remain in place without creeping. This is one of the advantages of this invention—that the orthodontist does not have to waste time holding a bracket until a conventional adhesive builds sufficient gel strength to hold the bracket in place. The next and subsequent brackets are then similarily treated and applied to the other teeth.

During the emplacement of brackets, a small amount of the bonding resin is ordinarily extruded from between the bracket base and the tooth surface around the edge of the bracket, illustrated by the cement 27, FIG. 3. This cement, or bonding resin, 27, is preferably folded over and around the edge of the bracket, illustrated by the dashed line 29, for better mechanical locking in place. If desired, additional catalyst may be dabbed over the resin 29 to ensure its polymerization into a durable bond.

By first applying the catalyst coating to the base of the bracket followed by applying the resin, polymerization is initiated immediately at the metal or plastic surface at the base of the bracket and the resin cures first at this location where initial bonding is most needed. Since the resin is applied adjacent the catalyst on the surface of the tooth, however, before the viscosity of the bulk of the resin is affected through polymerization, the viscosity to obtain the desired wetting of the tooth surface is correct. The reaction of polymerization adjacent the tooth surface is initiated only after contacting the coating of catalyst on the surface of the tooth. The result is that polymerization proceeds rapidly and a durable bond is effected between the two surfaces within about 10–25 minutes sufficient to allow attaching the remainder of the dental appliance. By localizing the action initially at the surfaces and by forcing the two surfaces into close proximity a very thin layer of resin occupies the space between the two surfaces and by virtue of the small mass there is rapid polymerization, producing strong bonds and consistent results; in contrast to the prior art methods.

The affixing of the remainder of the dental appliance is carried out by wiring with the high strength wires as has been done for many years and need not be described in great detail herein. Similarly, adjustments are made as conventional.

In the final step, when the orthodontic appliance is ready to be removed, the orthodontist may unwire the remainder of the appliance and employ snub-nosed gripper pliers to shear through the cement formed by the cured bonding resin. One of the advantages of this invention is that only about 5 percent of the bonding resin remains on the teeth; whereas with a conventional mixture about 50 percent (%) remains on the teeth. The total effect of this small residue is that much less time has to be spent polishing off the cement, or cured bonding resin, from the teeth with this invention.

ADDITIONAL EMBODIMENTS

One of the problems that has become evident in use of dental appliance has been the increased incidence of tooth decay. The orthodontists have become convinced that it would be helpful if there could be a sealant applied to the teeth before applying the orthodontic appliance. In accordance with another embodiment of this invention, such a thin layer of sealant can be effected without significantly altering the durable bond between the appliance and the tooth. The layer of sealant is effected by cleaning the teeth as described hereinbefore and applying a solution of the drying agent containing the catalyst. This allows the drying agent to vaporize to leave a layer of catalyst. Thereafter, a relatively thin layer of the bonding resin having a much lower viscosity in the range of 250–5,000 centipoises at room temperature is applied. Specifically, the bonding resin sealant is applied to the teeth. Warm, dry, clean air is blown over the layer of the bonding resin. If desired another layer of catalyst can be brushed over the outside. The one or two layers of catalyst then proceed to effect gellation and cure of the bonding resin rapidly to form a layer of sealant that is impervious to corrosive materials such as bacteria, enzymes, mouth acids and the like. The thin sealant fills the cracks and crevices. There may be srinkage of the bonding resin during polymerization but the layer of sealant remains intact. In the areas that are not exposed to daily teeth brushing or cleansing, the layer of the polymerized resin sealant is there to resist the effects of bacterial and calcareous decay.

The affixing of the dental appliance is carried out as described hereinbefore except that the layer of catalyst that is effected over the surfaces of the teeth has the layer of sealant interposed for protection. Adjustment and removal are carried out as described herein.

In the indirect bonding of the dental appliance to the teeth, a cast is made of the mouth of the patient and the brackets are temporarily affixed into the desired positions onto the cast. A layer of soft plastic such as polyethylene is folded over the brackets and vacuum drawn into place so as to embed the brackets in the soft plastic. Thereafter, the soft plastic containing the brackets are folded back and the embedded brackets are cleaned of the material used to temporarily affix the brackets to the teeth. A layer of catalyst is applied to the bases of the brackets. Also, a layer of catalyst is effected on the clean dry teeth, similarily as described hereinbefore. A layer of resin is then effected on the bracket bases. The plastic with the brackets embedded therein is inserted into the patients mouth such that the bracket bases are suitably emplaced adjacent the surfaces of the teeth to which they will bond. The plastic with the brackets emplaced is left in the patients mouth for a suitable interval of time to bond the brackets to the teeth. This time will be, for example, about 10 to 20 minutes. Thereafter, the plastic is removed to leave the brackets in place on the teeth in the patients mouth. This technique is done for speed in applying the brackets.

After the cure time of 10–20 minutes, the remainder of the dental appliance can be affixed. Adjustments and finally removal are carried out as described herein.

The following examples are given to illustrate in a very specific way this invention.

EXAMPLE 1

In this example the orthodontist first cleaned the teeth with a pumice type tooth paste and dried the teeth with warm, clean, dry air. Thereafter the orthodontist etched the teeth with a 37.5% solution of phosphoric acid. This solution was dabbed carefully onto the teeth with cotton pellets. This effected a clean acid etch. After allowing about one and a half minutes, the acid was thoroughly rinsed from the teeth and the teeth were again dried with dry air. A solution containing the drying agent and catalyst was brushed onto the teeth. The solvent evaporated with warm dry air in about 10 seconds. The solvent consisted of a 50—50 admixture of acetone and ethyl ether. The catalyst was benzoyl peroxide and constituted 5% of the solution.

Clean metal brackets that had been stored in a solution of the drying agent and the catalyst were arrayed on an absorbent towel so as to allow the drying agent to vaporize leaving a layer of catalyst on the bases of the brackets.

The bonding resin contained 1.2% initiator and 6.7% filler. The initiator was N,N-dimethyl-p-toluidine. The filler was fumed colloidal silica. The remainder of the resin was the resin monomer per se. The resin employed was a methacrylate-capped epoxy resin containing styrene amounting 45% of the mixture. The resin having the desired viscosity of about 32,000 centipoises measured at 50° C. temperature was applied by a spatula to the base of each metal bracket onto the layer of catalyst.

The metal bracket was firmly affixed to the tooth by means of tweezers, applying a firm force against each bracket in the exact position desired. After placement of the bracket on the tooth, the resin held the bracket in that position without allowing the bracket to creep. The excess bonding resin that was exuded from beneath the base of the bracket was folded around the edge of the bracket with a small spatula. The solution of benzoyl peroxide was again applied to the exposed surface of the bonding resin and particularly adjacent the edge of the brackets.

The remaining brackets were applied in the same manner.

Sufficient curing time was allowed; for example about 20 minutes; and the remainder of the appliance was affixed into place against each of the brackets to apply the desired force to affect the movement of the teeth in the desired way.

The orthodontist was thereafter able to make adjustments on the appliances that were applied to pull the teeth into positions desired. The teeth may be pushed or pulled with this method by using an external appliance.

When ready to be removed, the orthodontist employed snub-nosed gripper pliers and sheared through the cement formed by the cured resin. Only about 5% of total cement remained in place on the teeth. This cement was polished from the teeth and no ill effects were observed.

EXAMPLE 2

In this example, the same initial steps were employed for affixing the brackets to the teeth except that a thin layer of sealant was included as an additional step. The sealant was found helpful, since it minimized any decay or tendency of tooth decay under the orthodontic appliance. In applying the sealant, a thin layer of sealant was applied by first brushing on a solution of the catalyst, drying with warm air, then brushing on a thin layer of the monomer resin. Again the resin employed was a thin layer of methacrylate capped epoxy resin containing styrene having a viscosity of about 500 centipoises at 77° F. The thin layer was then dried by air and cured. After about 5 minutes another layer of catalyst was then applied over the cured layer of sealant after the time required for curing. The thin sealant apparently filled the cracks and crevises of the tooth and the epoxy sealant resisted bacterial attack that otherwise would have been made on calcareous tooth surfaces due to improper brushing during the time of the affixed dental appliance.

The remaining steps of applying the brackets and the dental appliance, making adjustments and removal were carried out as delineated hereinbefore in Example 1 except that the catalyst was applied, on a thin layer of sealant rather than on the tooth surfaces per se during attachment of the brackets. The same polymer resin used in Example 1 was employed. The sealant did not contain a filler.

EXAMPLE 3

The same procedure and steps were carried out in this example as were carried out in Example 1 except that the methacrylate capped epoxy resin contained diluent monomers other than styrene. One reactive diluent monomer was substituted for styrene in a series of resins with different reactive diluent monomers. For example reactive diluents used in the series were methyl methacrylate, hydroxy methyl methacrylate, ethylene glycol dimethylacrylate, diethylene glycol dimethacrylate, triethylene glycol dimethylacrylate, various polyethylene glycol methacrylates individually, trimethylol propane-trimethacrylate, 1,4-butane glycol dimethacrylate, 1,3-butane glycol dimethacrylate, n-propyl methacrylate, n-butyl methacrylate, penta-erythritol tetramethacrylate, and a few other methacrylate monomers. Each of these resins was found to provide a satisfactory bonding job.

EXAMPLE 4

The same procedure and steps were carried out in this example as were done in Example 3 except that another dimethacrylate was substituted for the methacrylate capped expoxy resin. For example polyethylene glycol methacrylate, trimethylol propane trimethacrylate, and penta-erythritol tetramethacrylate, and others were tested individually. The same individual reactive diluent monomers as given in Example 3 were used. In each case an acceptable adhesive system was demonstrated using the technique of applying brackets to teeth as described in Example 1. Also, the initiator, colloidal silica, and with and withoug a reactive monomer diluent was incorporated into each of the resins as described in Examples 1 and 3, with satisfactory results.

EXAMPLE 5

In this example, a cast is made of the mouth with the teeth as they exist in the mouth. The brackets are temporarily affixed in desired positions on the cast of the mouth. A soft plastic, such as polyethylene is folded over the brackets on the cast and vacuum-drawn into position. As a consequence, the brackets are embedded in the soft plastic and are removed from the cast.

In the usual steps, the drying agent containing the catalyst is brushed onto the clean bracket bases and onto the clean dry teeth and the respective bases and the teeth are dried as described in Example 1. The plastic is folded back to enable the brackets to be exposed and the bonding resin is emplaced on the bases of the brackets. The plastic, brackets and bonding resin are then emplaced over the teeth such that the brackets faithfully duplicate their respective positions on the mold. The plastic and affixed brackets are left in place for about 15 minutes to allow time for the resin to sufficiently cure. The plastic is then pealed from the brackets which are retained in place on the teeth. This indirect bonding procedure is thus acceptable for use with the adhesive technique described herein.

The orthodontic appliance is thereafter wired as desired and as described hereinbefore with final removal carried out as described in Example 1. This latter method is known as indirect bonding of the brackets to the teeth.

While the method and composition of this invention has been described hereinbefore directed primarily to the practice of orthodontia, it should be remembered that it may be employed for adhering directly to the teeth other dental appliances or the like. Specifically, such things as metal crowns, protective sheaths, space maintainers, bridges, peridontal splints, and other such dental appliances of a similar nature may be adhered directly to the teeth through the use of the two layers of the catalyst on, respectively, the dental appliance and the tooth with a layer of bonding resin between the two layers of catalyst.

Having thus described the invention, it will be understood that such description has been given by way of illustration and example and not by way of limitation, reference for the latter purpose being had to the appended claims.

What is claimed is:

1. A method of affixing to at least one tooth a dental appliance, comprising the steps of;
   a. effecting on a predetermined surface of the tooth to which a portion of a dental appliance is to be bonded a layer of catalyst that will effect polymerization of a bonding resin; said surface of said tooth being cleaned and dried so as to effect a good bond;
   b. effecting on a cleaned and dried surface of at least a portion of said dental appliance that is to be bonded to said tooth a layer of said catalyst that would effect polymerization of said bonding resin; said surface of said at least a portion of said dental appliance being that which is to be disposed adjacent and bonded to said tooth;
   c. applying intermediate said two layers of catalyst a layer of said bonding resin that will be polymerized by said catalyst and positioning said at least a portion of said dental appliance adjacent said surface of said tooth with the intermediate layer of resin between the two layers of catalyst on, respectively, said at least a portion of said dental appliance and said tooth surface so as to sandwich the thin layer of resin between the layers of catalyst and obtain polymerization of the resin and hence the necessary bonding of said at least a portion of the dental appliance to the surface of the tooth;
   d. after allowing a cure time interval for completion of the cure of said bonding resin sufficiently that said at least a portion of the dental appliance is firmly affixed to said tooth, affixing the remainder, if any, of said dental appliance; and
   e. a filler added to said resin to obtain the desired viscosity of said resin, to avoid creep and to obtain the desired wetability of the tooth and catalyst to said resin; said filler being present in a concentration in the range of 4–10 percent by weight.

2. The method of claim 1 wherein said filler is colloidal silica.

3. The method of claim 2 wherein said colloidal silica comprises fumed silica and is present in a concentration in the range of 6–7 percent by weight, inclusive.

4. A method of affixing to at least one tooth a dental appliance, comprising the steps of;
   a. effecting on a predetermined surface of the tooth to which a portion of a dental appliance is to be bonded a layer of catalyst that will effect polymerization of a bonding resin; said surface of said tooth being cleaned and dried so as to effect a good bond;
   b. effecting on a cleaned and dried surface of at least a portion of said dental appliance that is to be bonded to said tooth a layer of said catalyst that would effect polymerization of said bonding resin; said surface of said at least a portion of said dental appliance being that which is to be disposed adjacent and bonded to said tooth;
   c. applying intermediate said two layers of catalyst a layer of said bonding resin that will be polymerized by said catalyst and positioning said at least a portion of said dental appliance adjacent said surface of said tooth with the intermediate layer of resin between the two layers of catalyst on, respectively, said at least a portion of said dental appliance and said tooth surface so as to sandwich the thin layer of resin between the layers of catalyst and obtain polymerization of the resin and hence the necessary bonding of said at least a portion of the dental appliance to the surface of the tooth;
   d. after allowing a cure time interval for completion of the cure of said bonding resin sufficiently that said at least a portion of the dental appliance is firmly affixed to said tooth, affixing the remainder, if any, of said dental appliance;

said resin being hydrolysis-resistant and being selected from the class consisting of exoxy resin, urethane resin, cyano-acrylate resin, methacrylate resin, vinyl ester resin and polyacrylate resin.

5. The method of claim 4 wherein said catalyst of claim 1 is selected from the class consisting of benzoyl peroxide and methyl ethyl ketone peroxide.

6. The method of claim 4 wherein there is included in said resin an initiator selected from the class of N,N-dimethyl-p-toluidine, N,N-dimethylaniline and cobalt naphthenate.

7. The method of claim 6 wherein said initiator is present in a concentration within the range of 0.5–3.0 percent by weight.

8. The method of claim 7 wherein said initiator is present in a concentration within the range of 1.5–2.0 percent by weight.

9. A method of affixing a dental appliance to a plurality of brackets that are affixed to the respective surfaces of a plurality of teeth comprising the steps of:
   a. cleaning the surface of each of the teeth to which each respective said bracket is to be affixed;
   b. acidizing each surface of each said tooth to which each respective said bracket is to be affixed to create a cleanly etched surface on each said tooth;
   c. rinsing the acid etched surface of each said tooth to insure that it has been water washed and thoroughly cleaned;
   d. drying each said tooth with clean air;
   e. drying each said tooth with a drying agent and applying to the dried surface of each said tooth a layer of a catalyst that will effect polymerization of a bonding resin;
   f. cleaning the base of each said bracket;
   g. applying said catalyst to each said cleaned base of each said bracket;
   said bracket being stored in a drying solution of catalyst and drying agent as the method of applying said catalyst to the bracket bases, since when the drying agent evaporates the catalyst is left on the bases of said brackets;
   h. applying said bonding resin that will be polymerized by said catalyst to the layers of catalyst on said bracket bases;
   i. positioning said bracket adjacent said surfaces of said teeth with the intermediate layer of resin between the two layers of catalyst on, respectively, each respective bracket base and its tooth so as to sandwich each thin layer of bonding resin between the two layers of catalyst and obtain polymerization of the bonding resin and the necessary bonding of the brackets to the teeth; and
   j. after a predetermined cure time, affixing the remainder of said dental appliance to said brackets.

10. The method of claim 9 wherein said catalyst is present in a concentration within the range of 1–20 percent by weight of said drying solution.

11. The method of claim 9 wherein said drying agent is selected from the class consisting of ethyl alcohol, methyl ethyl ketone, acetone, ethyl ether, 2-methoxyethanol, 2-ethoxyethanol, 2-propoxyethanol and 2-butoxyethanol.

12. The method of claim 11 wherein said drying agent comprises a solution of ethyl alcohol and methyl ethyl ketone.

13. The method of claim 9 wherein silane is included in said drying solution.

14. The method of claim 9 wherein there is added to said bonding resin sufficient filler selected from the class consisting of particulate alumina, calcium fluoride, barium fluoride, glass, asbestos and silica; said particles having a predominant number of the particles in size up to 35 microns and having no particles so large as to interfere with the satisfactory bonding of said bracket base to said tooth surface; sufficient filler being employed to obtain said viscosity and avoid creep and obtain the desired wettability of the tooth surface to said resin for satisfactory bonding.

15. A method of affixing a dental appliance to teeth; said dental appliance including both brackets that are to be affixed to said teeth and the remainder of said dental appliance, and said brackets are affixed to said teeth by indirect bonding comprising the plurality of steps of;
   a. making a cast of the teeth and mouth of the patient;
   b. temporarily arranging the brackets on said cast;
   c. folding over said brackets a layer of soft plastic and embedding said brackets in said plastic;
   d. removing said plastic and brackets and applying a catalyst that will effect polymerization of a bonding resin on the bracket bases and the exterior surfaces of said teeth after said bracket bases and said teeth have been cleaned and dried;
   e. applying said bonding resin that will be polymerized by said catalyst to the bases of said brackets;
   f. inserting said plastic with said brackets in place and with said resin and catalyst on said bases into said mouth such that said brackets are emplaced with said resin adjacent the catalyst on the surfaces of said teeth and leaving said plastic with said brackets in place with said resin intermediate said layers of catalyst between the bracket base and the teeth and leaving for 10 to 20 minutes;
   g. removing said plastic to leave said bracket in place on said teeth; such that said teeth have said brackets affixed thereto; and
   h. allowing sufficient time for cure of said bonding resin and thereafter affixing the remainder of said dental appliance.

16. The method of claim 15 wherein said plastic comprises polyethylene plastic for embedding said brackets therein.

17. A method of affixing to at least one tooth a dental appliance, comprising the steps of;
   a. effecting on a predetermined surface of the tooth to which a portion of a dental appliance is to be bonded a layer of catalyst that will effect polymerization of a bonding resin; said surface of said tooth being cleaned and dried so as to effect a good bond;
   b. effecting on a cleaned and dried surface of at least a portion of said dental appliance that is to be bonded to said tooth a layer of said catalyst that would effect polymerization of said bonding resin; said surface of said at least a portion of said dental appliance being that which is to be disposed adjacent and bonded to said tooth;
   c. applying intermediate said two layers of catalyst a layer of said bonding resin that will be polymerized by said catalyst and positioning said at least a portion of said dental appliance adjacent said surface of said tooth with the intermediate layer of resin between the two layers of catalyst on, respectively, said at least a portion of said dental appliance and said tooth surface so as to sandwich the thin layer of resin between the layers of catalyst and obtain polymerization of the resin and hence the necessary bonding of said at least a portion of the dental appliance to the surface of the tooth;
   d. after allowing a cure time interval for completion of the cure of said bonding resin sufficiently that said at least a portion of the dental appliance is firmly affixed to said tooth, affixing the remainder, if any, of said dental appliance;
said bracket base and said surface of said tooth being selected to have matched curvatures.

18. A method of affixing to at least one tooth a dental appliance, comprising the steps of;
   a. effecting on a predetermined surface of the tooth to which a portion of a dental appliance is to be bonded a layer of catalyst that will effect polymerization of a bonding resin; said surface of said tooth being cleaned and dried so as to effect a good bond;
   b. effecting on a cleaned and dried surface of at least a portion of said dental appliance that is to be bonded to said tooth a layer of said catalyst that would effect polymerization of said bonding resin; said surface of said at least a portion of said dental appliance being that which is to be disposed adjacent and bonded to said tooth;
   c. applying intermediate said two layers of catalyst a layer of said bonding resin that will be polymerized by said catalyst and positioning said at least a portion of said dental appliance adjacent said surface of said tooth with the intermediate layer of resin between the two layers of catalyst on, respectively, said at least a portion of said dental appliance and said tooth surface so as to sandwich the thin layer of resin between the layers of catalyst and obtain polymerization of the resin and hence the necessary bonding of said at least a portion of the dental appliance to the surface of the tooth;
   d. after allowing a cure time interval for completion of the cure of said bonding resin sufficiently that said at least a portion of the dental appliance is firmly affixed to said tooth, affixing the remainder, if any, of said dental appliance;
said cure time interval being in the range of 10 minutes –2 hours.

19. The method of claim 18 wherein said cure time interval is 10–20 minutes.

20. A method of protecting teeth and affixing to the teeth a dental appliance, comprising the steps of:
   a. effecting on the cleaned and dried exposed surfaces of the teeth a layer of a catalyst that will effect polymerization of a resin to form a durably bonded layer of sealant on said teeth;
   b. effecting on the total exposed surfaces of said teeth a layer of resin having a viscosity in the range of 250–5,000 centipoises at room temperature; said resin being capable of being bonded into a durable layer of sealant for protection of said teeth;
   c. allowing said layers of catalyst and resin to interact to cure said resin and form said sealant;
   d. effecting on cleaned and dried predetermined surfaces of the teeth to which a portion of the orthodontic appliance is to be bonded respective layers of said catalyst;

e. effecting on respective cleaned and dried surfaces of at least a portion of the appliance that is to be bonded to said teeth respective layers of said catalyst;

f. applying intermediate said two layers of catalyst a layer of a resin having a viscosity in the range of 25,000-40,000 centipoises measured at 50° C.; said resin being adapted for curing into a durable bond; and positioning said at least a portion of said dental appliance adjacent said surfaces of said teeth with the intermediate layers of resin between the respective two layers of catalyst on, respectively, said appliance and said teeth surfaces so as to sandwich the thin layer of resin between the layers of catalyst and obtain the polymerization necessary to form the bond between the portion of the appliance and the surfaces of the teeth;

g. after allowing a cure time interval for completion of the cure of said bonding resin sufficiently that said at least a portion of said dental appliance firmly affixed to said teeth, affixing the remainder if any of said dental appliance.

21. The method of claim 20 when said resin is selected from the class consisting of hydroysis-resistant epoxy resin, urethane resin, cyano-acrylate resin, methacrylate resin, vinyl ester resin, and acrylate resin; and said catalyst is selected from the class consisting of benzoyl peroxide and methyl ethyl ketone peroxide.

22. The method of claim 21 wherein said resin includes an initiator selected from the class consisting of N,N-dimethyl-p-toluidine; N,N-dimethylaniline and cobalt naphthenate.

* * * * *